United States Patent
Bohn et al.

(10) Patent No.: US 6,469,033 B1
(45) Date of Patent: Oct. 22, 2002

(54) USE OF 1-HYDROXY-2-PYRIDONES FOR THE TREATMENT OF SKIN DISEASES

(75) Inventors: Manfred Bohn, Hofheim (DE); Karl Theodor Kraemer, Langen (DE); Astrid Markus, Liederbach (DE)

(73) Assignee: Aventis Pharma Deutschland GmbH, Frankfurt (DE)

( * ) Notice: Subject to any disclaimer, the term of this patent is extended or adjusted under 35 U.S.C. 154(b) by 0 days.

(21) Appl. No.: 09/077,191

(22) PCT Filed: Sep. 16, 1997

(86) PCT No.: PCT/EP97/05069

§ 371 (c)(1),
(2), (4) Date: Aug. 20, 1998

(87) PCT Pub. No.: WO98/13043

PCT Pub. Date: Apr. 2, 1998

(30) Foreign Application Priority Data

Sep. 27, 1996 (DE) .......................... 196 39 817

(51) Int. Cl.[7] .............................................. A01N 43/40
(52) U.S. Cl. ...................................... 514/345; 514/350
(58) Field of Search .................................. 514/345, 350

(56) References Cited

U.S. PATENT DOCUMENTS

| | | | |
|---|---|---|---|
| 3,968,118 A | 7/1976 | Lohaus et al. .............. | 260/297 |
| 4,185,106 A | 1/1980 | Dittmar et al. ............. | 424/263 |
| 4,797,409 A | * 1/1989 | Lohaus et al. .............. | 514/345 |
| 4,957,730 A | 9/1990 | Bohn et al. .................. | 424/61 |
| 5,066,484 A | 11/1991 | Castrogiovanni et al. ..... | 424/61 |
| 5,120,530 A | 6/1992 | Ferro et al. .................. | 424/61 |
| 5,132,107 A | 7/1992 | Lange ......................... | 424/70 |
| 5,264,206 A | 11/1993 | Bohn et al. .................. | 424/61 |
| 5,346,692 A | 9/1994 | Wohlrab et al. .............. | 424/61 |
| 5,494,658 A | 2/1996 | Hänel et al. ................ | 424/70.1 |
| 5,603,939 A | 2/1997 | Ser ............................ | 424/401 |
| 5,650,145 A | 7/1997 | Saint-Leger ................ | 424/70.1 |
| 5,675,013 A | 10/1997 | Hani et al. .................. | 514/348 |
| 5,683,681 A | 11/1997 | Ramin et al. ................ | 424/61 |
| 5,753,600 A | 5/1998 | Kamegai et al. ............ | 510/131 |
| 5,866,105 A | 2/1999 | Richter et al. | |
| 6,162,420 A | 12/2000 | Bohn et al. .................. | 424/61 |

FOREIGN PATENT DOCUMENTS

| | | |
|---|---|---|
| CA | 2134293 | 4/1995 |
| DE | 31 40954 A1 | 5/1983 |
| DE | 38 26 914 A1 | 2/1990 |
| EP | 0 218 410 A2 | 4/1987 |
| EP | 0 241 918 A2 | 10/1987 |
| EP | 0 313 305 | 4/1989 |
| EP | 0 381 446 A1 | 8/1990 |
| EP | 0 515 312 A2 | 11/1992 |
| EP | 0 646 369 A1 | 4/1995 |
| EP | 0 649 660 A2 | 4/1995 |
| EP | 0 680 745 A2 | 11/1995 |
| EP | 0 680 745 A3 | 11/1995 |
| EP | 0 771 187 B1 | 5/1997 |
| FR | 2 618 068 | 1/1989 |
| FR | 2 685 638 | 7/1993 |
| FR | 2 685 867 A1 | 7/1993 |
| FR | 2 694 694 A1 | 2/1994 |
| FR | 0771 187 B1 | * 10/1998 |
| GB | 2 208 149 A | 3/1989 |
| GB | 2208149 A | * 3/1989 |
| HU | 202098 | 3/1990 |
| JP | 61-69721 | 4/1986 |
| WO | WO 87 02580 | 5/1987 |
| WO | 94/05256 | 3/1994 |
| WO | WO 96/13247 | 4/1995 |
| WO | 95/17165 | 6/1995 |
| WO | 96/2226 A1 | 2/1996 |
| WO | WO 96 19186 | 6/1996 |
| WO | WO 96 29045 | 9/1996 |
| WO | 96/29056 | 9/1996 |
| WO | WO 99 39680 | 8/1999 |
| WO | WO 99 49835 | 10/1999 |

OTHER PUBLICATIONS

Raether et al., "Rilopirox–a New Hydroxypyridone Antifungal with Fungicidal Properties," Mycoses, Bd. 33, No. 4, pp. 191–202, Apr. 5, 1990.*
Translation of FR 2,685,867, Jul. 9, 1993.*
Translation of EP 0 771 187.
Rivalland, P., "Evaluation of the Antifungal of Two Derivatives and In Vivo Innocuity Test of Shampooings with Regard to Antidandruff Formulations," Abstract, Int. J. Cosmet. Sci. (1994), vol. 16(2), pp. 77–83.
Abstract of FR 2 685 867 A1.
Abstract of FR 2 694 694 A1.
Yoshimasa et al., The sebum lipid assimilation and the growth inhibition of *Pityrosporum ovale*(1st report), J. SCCJ, vol. 22(3), pp. 165–170 (1988).
Saint–Leger et al., The role of the resident microflora in the pathogenesis of dandruff, J. Soc. Cosmet. Chem., vol. 40, pp. 109–117 (1989).
Martindale The Extra Pharmacopoeia 30th Ed., London The Pharmaceutical Press 1993, pp. 332, 1609.

(List continued on next page.)

Primary Examiner—Dway C. Jones
(74) Attorney, Agent, or Firm—Finnegan, Henderson, Farabow, Garrett & Dunner LLP

(57) ABSTRACT

Compounds of the formula I

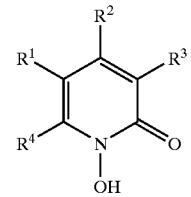

(I)

are suitable for the production of pharmaceuticals for the topical treatment of skin infections which are caused by fungi and bacteria.

7 Claims, No Drawings

OTHER PUBLICATIONS

Montana, et al., "A Double–Blind, Vehicle–Controlled Study of the Safety and Efficacy of Fungoid Tincture® in Patients with Distal Subungual Onychmycosis of the Toes," *Cutis*, 53:313–316 (1994).

Derwent Abstract of FR 2 618 068, Jan. 20, 1989.

Derwent Abstract of JP 61–69721, Apr. 10, 1986.

Derwent Abstract of DE 3826914 A1, Feb. 15, 1990.

English translation of Abstract for E. Grosshans et al., "L'Eczema Seborrheique (La Pityrosporose)," Ann. Dermatol. Venereol., 115:79–86, 1988.

Derwent Abstract of FR 2 685 638, 1993.

Derwent Abstract of DE 31 40954 A1, 1983.

Derwent Abstract of WO 96/2226A1, 1996.

H. Hanel et al., "Treatment of seborrhoic eczema using an antimycotic with antiphlogistic properties," *Mycoses*, 34 Suppl. 91–93 (1991), Aug. 31, 1991.

J. Shapiro et al., "Medicated Shampoos," *Clinics in Dermatology*, 14:123–128, 1996.

R. Aly et al., "Common Superficial Fungal Infections in Patients with AIDS," *CID* 22, Supp. 2, pp. 128–132, 1996.

Japanese Abstract No. 07082126–A, vol. 95, No. 003, Mar. 28, 1995.

H. Hanel et al., "Evaluation of Fungicidal Action in Vitro and in a Skin Model Considering the Influence of Penetration Kinetics of Various Standard Antimycotics," *Annals New York Academy of Sciences*, vol. 544, pp. 329–337, 1988.

P.C. Braga et al., "Inhibition of *Candida albicans* Adhesiveness to Human Buccal and Vaginal Cells by Sub–inhibitory Concentrations of Rilopirox," *Arzneim.–Forsch./Drug Res.*, vol. 45, No. 1, pp. 84–87, 1995.

W. Raether et al., "Rilopirox–a New Hydroxypyridone Antifungal with Fungicidal Properties," *Mycoses*, Bd. 33, No. 4, pp. 191–202, Apr. 5, 1990.

H. Hanel et al., "A Comparison of Bifonazole and Ciclopiroxolamine: In Vitro, Animal, and Clinical Studies," *Mycoses 31*, No. 12, pp. 632–640, Oct. 13, 1988.

\* cited by examiner

USE OF 1-HYDROXY-2-PYRIDONES FOR THE TREATMENT OF SKIN DISEASES

This application is a 371 of PCT/EP 97/05069 filed Sep. 16, 1997.

Infections of the skin are caused to a vast extent by skin-pathogenic bacteria or fungi. Their treatment—depending on the particular pathogen—is carried out either using antibacterial or using antimycotic agents.

Staphylococci and streptococci are a cause of bacterial infections of the skin in about 70% of all cases. Further important pathogens of bacterial skin infections which may be mentioned are Proteus sp. Other bacteria which grow under aerobic and anaerobic conditions, such as enterococci, *Escherichia coli, Pseudomonas aeruginosa* and *Klebsiella* come into question far less frequently as pathogens of skin infections.

Yeasts, on the other hand, have recently markedly gained in importance as pathogens of skin infections, in particular in immunosuppressed patients, in which the mucocutaneous and systemic spread of the yeasts can be a therapeutic problem.

Since bacteria as a rule have no noticeable keratinase activity, which is necessary for the start of an infection, fungal infections are frequently a starting point for the emergence of bacterial secondary infections.

The present invention therefore relates to substances which are suitable for the topical treatment both of fungal infections and of bacterial infections of the skin. Topical wide-spectrum antiinfectives according to the present invention were until now not available as monopreparations for the treatment of skin infections.

In the choice of agents for antibacterial therapy, inter alia, development of resistance must in particular be taken into consideration. Especially in the case of longer treatment, the pathogen spectrum should be determined by wound smears and its behavior checked with respect to the compositions used. Furthermore, note must be made of contact sensitivities and intolerability reactions. Especially in the case of neomycin and gentamycin, which have been used for many years in the treatment of skin infections, the danger of sensitization is high.

For staphylococcal infections of the skin, which are frequent everywhere, erythromycin and clindamycin are frequently also employed in addition to gentamycin. They are used both locally, mainly in acne therapy, and also systemically.

However, owing to systemic administration, which has been carried out for many years, therapy-resistant bacterial strains have developed both against gentamycin and against erythromycin and clindamycin to a great extent—even against modern gyrase inhibitors, such as, for example, ofloxacin. In a retrospective study, Th. Forssmann et al. (H+G Volume 69, Part 12, 1994, pp. 828–832) analyzed the antibiotic resistance of *Propionibacterium acnes* and *Staphylococcus epidermidis* in acne patients who were pretreated with antibiotics.

The investigations show that, with respect to Propionibacteria, resistances were found to erythromycin in 36% and to clindamycin in 11% of the cases. With *Staphylococcus epidermidis*, resistances were found to erythromycin in 90% and to clindamycin in 40% of the cases.

The increasing number of resistances of enterococci to gentamycin (up to 50% in isolates from various centers) gives reason to think particularly the same strains also are resistant to many other substances, including vancomycin (Martindale 30th Edition, 1993, pp. 171,2).

The same problem exists with gentamycin-resistant *Staphylococcus aureus* strains, which as a rule are also insensitive to methicillin and ofloxacin (Martindale 30th Edition, 1993, pp. 171,2 own investigations).

It is furthermore known from the literature that among the conventional antibiotics cross-resistances are developing to an increasing extent. Thus, inter alia, in the case of patients who were only pretreated with erythromycin, in 20% of the cases a resistance to clindamycin was also observed.

For the reasons outlined, it no longer applies as a therapeutic standard today also to employ topically antibiotics which are used systemically.

In the search for a new therapeutic standard for antibiotically active substances to be used topically, it has now surprisingly been found that substances from the 1-hydroxy-2-pyridone class, which until now have found their way into therapy exclusively as antimycotics, are also excellently suited for the topical treatment of bacterial skin infections.

In more recent experiments, it was possible, in particular, to show that 1-hydroxy-2-pyridones have an uninterrupted spectrum of action against the bacterial species occurring in skin infections, in particular also against antibiotic-resistant strains. In combination with the already-known antimycotic properties of the 1-hydroxy-2-pyridones, this is an extremely important finding for the successful treatment of skin infections, as the hitherto obligatory bacterial identification with subsequent resistance testing on treatment with the substances according to the invention is no longer necessary, which in the end also leads, inter alia, to a substantial reduction in the treatment costs.

The invention therefore relates to the use of 1-hydroxy-2-pyridones of the formula I

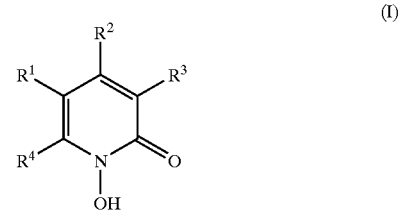

in which
$R^1$, $R^2$ and $R^3$, which are identical or different, are a hydrogen atom or alkyl having 1–4 carbon atoms, and
$R^4$ is a saturated hydrocarbon radical having 6 to 9 carbon atoms or a radical of the formula II

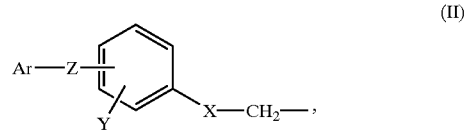

where
X is S or O,
Y is a hydrogen atom or up to 2 halogen atoms such as chlorine and/or bromine,
Z is a single bond or the divalent radicals O, S, —CR$_2$ (R=H or ($C_1$–$C_4$)-alkyl) or other divalent radicals having 2–10 carbon and optionally O and/or S atoms linked in the form of a chain, where—if the radicals contain 2 or more O and/or S atoms—the latter must be separated from one another by at least 2 carbon atoms and where 2 adjacent carbon atoms can also be linked to one another by a double bond and the free valencies of the carbon atoms are saturated by H and/or ($C_1$–$C_4$)-alkyl groups, Ar is an aromatic ring system having up to two rings which can be substituted by up to three radicals from the group consisting of fluorine, chlorine, bromine, methoxy, ($C_1$–$C_4$)-alkyl, trifluoromethyl and trifluoromethoxy in free or in salt form, for the production of a pharmaceutical for the topical treatment of skin infections which are caused by fungi and bacteria.

In the radicals "Z", the carbon chain members are preferably $CH_2$ groups. If the $CH_2$ groups are substituted by $C_1$–$C_4$ alkyl groups, $CH_3$ and $C_2H_5$ are preferred substituents. Exemplary radicals "Z" are:

—O—, —S—, —$CH_2$—, —$(CH_2)_m$— (m=2–10), —C($CH_3$)$_2$—, —$CH_2$O—, —O$CH_2$—, —$CH_2$S—, —S$CH_2$—, —SCH($C_2H_5$)—, —CH=CH—$CH_2$O—, —O—$CH_2$—CH=CH—$CH_2$O—, —O$CH_2$—$CH_2$O—, —O$CH_2$—$CH_2CH_2$O—, —S$CH_2$$CH_2$$CH_2$S—, —S$CH_2$$CH_2$$CH_2$$CH_2$O—, —S$CH_2$$CH_2$O$CH_2$$CH_2$O—, —S$CH_2$$CH_2$O$CH_2$$CH_2$O—$CH_2$$CH_2$S— or —S—$CH_2$—C($CH_3$)$_2$—$CH_2$—S—.

The radical "S" denotes a sulfur atom, the radical "O" denotes an oxygen atom. The term "Ar" denotes phenyl or condensed systems such as naphthyl, tetrahydronaphthyl and indenyl, and also isolated systems such as those which are derived from biphenyl, diphenylalkanes, diphenyl ethers and diphenyl thioethers.

In the formula I, the hydrocarbon radical $R^4$ is an alkyl or cyclohexyl radical which can also be bonded to the pyridone ring via a methylene or ethylene group or can contain an endomethyl group. $R^4$ can also be an aromatic radical which, however, is preferably bonded to the pyridone radical via at least one aliphatic carbon atom.

Important representatives of the class of compound characterized by the formula I are:

6-[4-(4-chlorophenoxy)phenoxymethyl]-1-hydroxy-4-methyl-2-pyridone, 6-[4-(2,4-dichlorophenoxy)phenoxymethyl]-1-hydroxy-4-methyl-2-pyridone, 6-(biphenylyl-4-oxymethyl)-1-hydroxy-4-methyl-2-pyridone, 6-(4-benzyl-phenoxymethyl)-1-hydroxy-4-methyl-2-pyridone, 6-[4-(2,4-dichlorobenzyloxy)phenoxymethyl]-1-hydroxy-4-methyl-2-pyridone, 6-[4-(4-chlorophenoxy)phenoxymethyl]-1-hydroxy-3,4-dimethyl-2-pyridone, 6-[4-(2,4-dichlorobenzyl)phenoxymethyl]-1-hydroxy-3,4-dimethyl-2-pyridone, 6-[4-(cinnamyloxy)phenoxymethyl]-1-hydroxy-4-methyl-2-pyridone, 1-hydroxy-4-methyl-6-[4-(4-trifluoromethylphenoxy)phenoxymethyl]-2-pyridone, 1-hydroxy-4-methyl-6-cyclohexyl-2-pyridone, 1-hydroxy-4-methyl-6-(2,4,4-trimethylpentyl)-2-pyridone, 1-hydroxy-4-methyl-6-n-hexyl-, -6-iso-hexyl-, -6-n-heptyl- or -6-iso-heptyl-2-pyridone, 1-hydroxy-4-methyl-6-octyl- or -6-iso-octyl-2-pyridone, in particular 1-hydroxy-4-methyl-6-cyclohexylmethyl- or -6-cyclohexylethyl-2-pyridone, where the cyclohexyl radical in each case can also carry a methyl radical, 1-hydroxy-4-methyl-6-(2-bicyclo[2,2,1]heptyl)-2-pyridone, 1-hydroxy-3,4-dimethyl-6-benzyl- or -6-dimethylbenzyl-2-pyridone or 1-hydroxy-4-methyl-6-(β-phenylethyl)-2-pyridone.

The term "saturated" here designates those radicals which contain no aliphatic multiple bonds, i.e. no ethylenic or acetylenic bonds. The term "topical" is understood as meaning the local action on the skin. The term "fungus" means all chlorophyll-free cells with cellulose or chitin in the cell walls which contain chromosomes in the cell nucleus. The fungi in particular include yeast, mold fungi, skin, hair and budding fungi. The term "bacteria" means microorganisms with heterotrophic or autotrophic metabolisms, which have no chromosomal nucleus. The bacteria include gram-positive and gram-negative microorganisms, in particular those which can grow on the skin surface of humans or animals, for example skin-pathogenic bacteria of the genera staphylococci, streptococci, corynebacteria, propionibacteria and Proteus, and also other aerobic and anaerobically growing bacteria such as enterococci, *Escherichia coli*, Pseudomonas and Klebsiella. The term "antibiotic resistance" means the property of microorganisms to be insensitive to the therapeutically achievable active compound concentration of an active compound.

The abovementioned compounds of the formula I can be employed both in free form and as salts; use in free form is preferred.

If organic bases are used, poorly volatile bases are preferably employed, for example low molecular weight alkanolamines such as ethanolamine, diethanolamine, N-ethylethanolamine, N-methyldiethanolamine, triethanolamine, diethylaminoethanol, 2-amino-2-methyl-n-propanol, dimethylaminopropanol, 2-amino-2-methylpropanediol, triisopropanolamine. Further poorly volatile bases which may be mentioned are, for example, ethylenediamaine, hexamethylenediamine, morpholine, piperidine, piperazine, cyclohexylamine, tributylamine, dodecylamine, N,N-dimethyldodecylamine, stearylamine, oleylamine, benzylamine, dibenzylamine, N-ethylbenzylamine, dimethylstearylamine, N-methylmorpholine, N-methylpiperazine, 4-methylcyclohexylamine, N-hydroxyethylmorpholine. The salts of quaternary ammonium hydroxides such as trimethylbenzylammonium hydroxide, tetramethylammonium hydroxide or tetraethylammonium hydroxide can also be used, and furthermore guanidine and its derivatives, in particular its alkylation products. However, it is also possible to employ, for example, low molecular alkylamines such as methylamine, ethylamine or triethylamine as salt-forming agents. Salts with inorganic cations, for example alkali metal salts, in particular sodium, potassium or ammonium salts, alkaline earth metal salts such as in particular the magnesium or calcium salts, and salts with di- to tetravalent cations, for example the zinc, aluminum or zirconium salt, are also suitable for the compounds to be employed according to the invention.

The active compounds of the formula I to be employed in the preparations can be prepared, for example, by the process according to U.S. Pat. No. 2,540,218.

For use according to the invention of the compounds mentioned, liquid to semisolid pharmaceutical preparations are suitable, in particular solutions, cream, ointment and gel preparations, where the latter are preferably used because of their increased release of active compound. The production of these preparations is carried out in a manner known per se with addition of the active compound employed according to the invention. Of the abovementioned 1-hydroxy-2-pyridones, the preparations according to the invention can contain one compound or alternatively two or more in combination.

In the preparations according to the invention, the active compound is incorporated in amounts which are customarily between approximately 0.1 and approximately 5%, preferably between 0.5 and 1%.

Using the pharmaceuticals according to the invention, a drastic cure can be achieved in the topical treatment of infections of the skin. The compositions according to the invention can also be employed for the treatment of acne, rosacea—a disease of still unclarified etiology—and of erythrasma, a pseudomycosis of the skin caused by *Corynebacterium minutissimum*.

EXAMPLE 1

A preparation according to the invention has the following composition:

| | |
|---|---|
| 1-Hydroxy-4-methyl-6-(2,4,4-trimethylpentyl)-2-(1H)pyridone | 0.50% |
| Hydroxyethylcellulose | 1.50% |
| Polyethylene glycol-7 glycerylcocoate | 5.00% |
| 1,2-Propylene glycol | 10.00% |
| Isopropyl alcohol | 20.00% |
| Demineralized water | 63.00% |

EXAMPLE 2

A preparation according to the invention has the following composition:

| | |
|---|---|
| 1-Hydroxy-4-methyl-6-cyclohexyl-2(1H)pyridone | 1.00% |
| Polyacrylic acid polymer (e.g. Carbomer 940) | 0.70% |
| Sodium hydroxide | 0.20% |
| Sodium dioctylsulfosuccinate | 0.05% |
| 2-Octyldecanol | 7.50% |
| Isopropyl alcohol | 25.00% |
| Demineralized water | 65.55% |

EXAMPLE 3

A preparation according to the invention has the following composition:

| | |
|---|---|
| 1-Hydroxy-4-methyl-6-cyclohexyl-2(1H)pyridone | 0.50% |
| Polyacrylic acid polymer (e.g. Carbomer 940) | 0.50% |
| Sodium hydroxide | 0.20% |
| Polyoxyethylene(20) sorbitan monostearate | 3.50% |
| Isopropyl myristate | 10.00% |
| Ethanol | 20.00% |
| Demineralized water | 65.30% |

EXAMPLE 4

A preparation according to the invention has the following composition:

| | |
|---|---|
| 1-Hydroxy-4-methyl-6-(2,4,4-trimethylpentyl)-2(1H)-pyridone | 1.00% |
| Hydroxypropylcellulose | 1.00% |
| 1,2-Propylene glycol | 2.50% |
| Ethanol | 20.00% |
| Demineralized water | 75.50% |

EXAMPLE 5

A preparation according to the invention has the following composition:

| | |
|---|---|
| 1-Hydroxy-4-methyl-6-cyclohexyl-2(1H)pyridone | 1.00% |
| Isopropyl alcohol | 25.00% |
| Polyethylene glycol 400 | 5.00% |
| Demineralized water | 69.00% |

EXAMPLE 6

A preparation according to the invention has the following composition:

| | |
|---|---|
| 1-Hydroxy-4-methyl-6-(trimethyl-pentyl-2(1H)pyridone | 1.00% |
| 2-Octyldocenol | 5.00% |
| Liquid paraffin | 5.00% |
| Cetyl alcohol | 5.00% |
| Stearyl alcohol | 5.00% |
| Myristyl alcohol | 5.00% |
| Polyoxyethylene-20-sorbitan monostearate | 3.00% |
| Sorbitan monostearate | 2.00% |
| Demineralized water | 69.00% |

EXAMPLE 7

Activity Testing

Determination of the antibacterial activity of 1-hydroxy-4-methyl-6-cyclohexyl-2(1H)pyridone to skin-pathogenic gram-positive and gram-negative aerobic bacteria.

The minimal inhibitory concentration (MIC) was determined in an agar dilution test in Mueller-Hinton agar. The active compound was first dissolved in dimethyl sulfoxide at 10% strength and then diluted to twice the amount in each case in equal stages with agar so that in the end effect concentrations between 128 µg/ml and 1 µg/ml were obtained. Overnight cultures of the bacterial strains to be tested were diluted with liquid medium and employed as inoculum. The bacterial suspensions ($1 \times 10^5$ cfu/ml) were applied to the surface of the active compound-containing agar plates. With the exception of the methicillin-resistant strains of *Staphylococcus aureus* (MRSA) and *Staphylococcus epidermidis* (MRSE), the MIC values were read off after 24 hours at 37° C.(MRSA and MRSE: 48 hours at 30° C.).

The lowest concentration at which growth was no longer to be observed was designated as the MIC.

Using known methods, the antibiotic-resistant bacteria investigated can be isolated from patients or from hospitals in which antibiotic resistance has been found. The other bacterial species mentioned can be isolated easily by a person skilled in the art on account of their species and generic name or ordered from a strain collection.

Results

In vitro activity of 1-hydroxy-4-methyl-6-cyclohexyl-2 (1H)pyridone against aerobic bacteria

| | n = | MIC (µg/ml) (n =) |
|---|---|---|
| Gram-positive strains | | |
| *Staphylococcus aureus* | 20 | 64 |
| *S. aureus*, methicillin-resistant MRSA | 19 | 64 |
| *S. aureus*, ofloxacin-resistant, OFX$^r$ | 16 | $64_{(8)}, 128_{(8)}$ |

-continued

| | n = | MIC (μg/ml) (n =) |
|---|---|---|
| *Staphylococcus epidermidis* | 20 | 128 |
| *S. epidermidis*, methicillin-resistant, MRSE | 2 | 64 |
| *S. epidermidis*, ofloxacin-resistant, OFX$^r$ | 4 | 64 |
| *Streptococcus pyogenes* | 20 | 64 |
| *Strept. faecalis* | 3 | 64$_{(1)}$, 128$_{(2)}$ |
| *Strept. faecium* | 1 | 128 |
| *Strept. faecium*, vancomycin-resistant, VAN$^r$ | 1 | 32 |
| *Strept. durans* | 10 | 64$_{(4)}$, 128$_{(6)}$ |
| *Strept. equisimilis* | 1 | 128 |
| *Strept. agalactiae* | 9 | 128 |
| Gram-negative strains | | |
| *Proteus vulgaris* | 3 | 32$_{(1)}$, 64$_{(2)}$ |
| *Enterobacter aerogenes* | 1 | 128 |
| *Enterobacter cloacae* | 1 | 128 |
| *Escherichia coli* | 3 | 64 |
| *Klebsiella pneumoniae* | 2 | 64$_{(1)}$, 128$_{(1)}$ |
| *Pseudomonas aeruginosa* | 5 | 128 | n = number of strains investigated; the number mentioned in brackets gives the tested strains in which the MIC mentioned was determined.

In vitro activity of 1-hydroxy-4-methyl-6-cyclohexyl-2 (1H)pyridone against anaerobic bacteria (the testing was carried out in an agar dilution test using Wilkins-Chalgren agar (Oxoid).

| Description of bacteria | | MIC (μg/ml) |
|---|---|---|
| *Propionibacterium acnes* | Strain 6919 | 32.0 |
| *Propionibacterium acnes* | Strain 6922 | 32.0 |
| *Propionibacterium acnes* | Strain 15549 | 32.0 |
| *Propionibacterium acnes* | Strain DSM 20458 | 32.0 |

All bacterial strains tested are inhibited in growth—without exception—in a very narrow concentration range of 1-hydroxy-2-pyridones. This also applies to strains which are resistant against therapy with antibiotics such as methicillin, ofloxacin and vancomycin.

What is claimed is:

1. A method of treating a human or animal patient in need of treatment for a skin infection, which is caused, at least in part, by at least one antibiotic-resistant bacterium, the method comprising applying to the skin infection of the patient an efficacious amount of at least one compound chosen from 1-hydroxy-2-pyridones of formula I and pharmaceutically acceptable salts thereof:

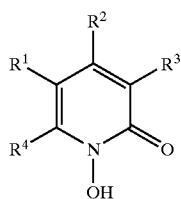

(I)

where $R^1$, $R^2$, and $R^3$, which are identical or different, are H or alkyl having 1 to 4 carbon atoms, and $R^4$ is a saturated hydrocarbon radical having 6 to 9 carbon atoms or a radical of formula II:

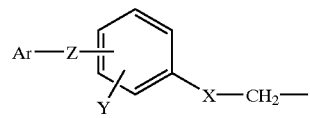

(II)

where:
X is S or O;
Y is H, or up to 2 halogen atoms;
Z is a single bond, or a bivalent radical comprising
  (1) O, or
  (2) S, or
  (3) —CR$_2$—, where R is H or (C$_1$–C$_4$)-alkyl, or
  (4) from 2 to 10 carbon atoms linked in the form of a chain, which optionally further comprises one or more of the following:
    (i) a carbon-carbon double bond, or
    (ii) O, S, or a mixture thereof, wherein if 2 or more O or S atoms or a mixture thereof are present, each O or S atom is separated by at least 2 carbon atoms; and,
  in any of the foregoing bivalent radicals, the free valences of the carbon atoms of said bivalent radical are saturated by H, (C$_1$–C$_4$)-alkyl, or a mixture thereof; and
Ar is an aromatic ring system having one or two rings, wherein the system is unsubstituted or substituted by one, two, or three radicals, which are identical or different, and are chosen from halogen, methoxy, (C$_1$–C$_4$)-alkyl, trifluoromethyl, and trifluoromethoxy.

2. A method of treating a human or animal patient in need of treatment for a skin infection, which is caused, at least in part, by at least one antibiotic-resistant bacterium, as claimed in claim 1, wherein the at least one antibiotic-resistant bacterium is chosen from gram-positive and gram-negative microorganisms.

3. A method of treating a human or animal patient in need of treatment for a skin infection, which is caused, at least in part, by at least one antibiotic-resistant bacterium, as claimed in claim 1, wherein the at least one antibiotic-resistant bacterium is chosen from skin-pathogenic bacteria from the genera Staphylococci, Streptococci, Proteus, Corynebacteria, and Propionibacteria.

4. A method of treating a human or animal patient in need of treatment for a skin infection, which is caused, at least in part, by at least one antibiotic-resistant bacterium, as claimed in claim 1, wherein the at least one antibiotic-resistant bacterium is chosen from bacteria which grow aerobically or anaerobically.

5. A method of treating a human or animal patient in need of treatment for a skin infection, which is caused, at least in part, by at least one antibiotic-resistant bacterium, as claimed in claim 1, in which the skin infection is caused, at least in part, by at least one bacterium chosen from *Escherichia coli*, Enterococci, Pseudomonas, and Klebsiella.

6. A method of treating a human or animal patient in need of treatment for a skin infection, which is caused, at least in part, by at least one antibiotic-resistant bacterium, as claimed in claim 1, in which the skin infection is acne, rosacea, or erythrasma.

7. A method of treating a human or animal patient in need of treatment for a skin infection, which is caused, at least in part, by at least one antibiotic-resistant bacterium, as claimed in claim 1, in which the 1-hydroxy-2-pyridone is topically applied to the skin infection.

* * * * *